United States Patent [19]

Labroo et al.

[11] Patent Number: 5,416,098
[45] Date of Patent: May 16, 1995

[54] METHOD FOR TREATING DERMATITIS AND RELATED CONDITIONS

[75] Inventors: Virender M. Labroo, Mill Creek; James R. Piggott, Bothell, both of Wash.

[73] Assignee: ZymoGenetics, Inc., Seattle, Wash.

[21] Appl. No.: 175,840

[22] Filed: Dec. 30, 1993

[51] Int. Cl.⁶ .................. A61K 31/395; A61K 31/55; A61K 31/445; A61K 31/40

[52] U.S. Cl. .................................. 514/320; 514/210; 514/212; 514/422; 514/861; 514/863

[58] Field of Search ............... 514/320, 861, 863, 456, 514/210, 212, 422

[56] References Cited

U.S. PATENT DOCUMENTS

| | | | |
|---|---|---|---|
| 4,644,012 | 2/1987 | Tsuda et al. | 514/456 |
| 4,742,066 | 5/1988 | Deckner et al. | 514/311 |
| 4,851,433 | 7/1989 | Kraus | 514/648 |
| 4,885,309 | 12/1989 | Welton | 514/456 |
| 5,248,777 | 9/1993 | Chandraratna | 546/165 |
| 5,254,568 | 10/1993 | Kapil et al. | 514/320 |

FOREIGN PATENT DOCUMENTS

92/18481 10/1992 WIPO .
92/20642 10/1992 WIPO .
93/20058 10/1993 WIPO .
93/20059 10/1993 WIPO .

OTHER PUBLICATIONS

Veigl et al., *Pharmac. Ther.* 44: 181–239, 1989.
Dhawan et al., *Br. J. Pharmac.* 49: 64–73, 1973.
Neil et al., *Br. J. Derm.* 128: 143–150, 1993.
Saeed et al., *J. Med. Chem.* 33: 3210–3216, 1990.
Sharma et al., *J. Med. Chem.* 33: 3222–3229, 1990.
Sharma et al., *J. Med. Chem.* 33: 3216–3222, 1990.
Ray et al., *J. Med. Chem.* 19: 276–279, 1976.
Wiseman, *Trends in Pharmacol. Sci.* 15: 83–89, 1994.

*Primary Examiner*—Marianne M. Cintins
*Assistant Examiner*—Kimberly R. Jordan
*Attorney, Agent, or Firm*—Gary E. Parker; Deborah A. Sawislak

[57] ABSTRACT

Methods and pharmaceutical compositions for the treatment of dermatitis are disclosed. 2,3-diaryl-1-benzopyrans and their pharmaceutically acceptable salts are formulated into medicaments, including oral and topical medicaments, which are administered to a patient suffering from dermatitis. The methods and compositions are particularly useful in the treatment of conditions characterized by hyperproliferation of keratinocytes, such as psoriasis.

13 Claims, 1 Drawing Sheet

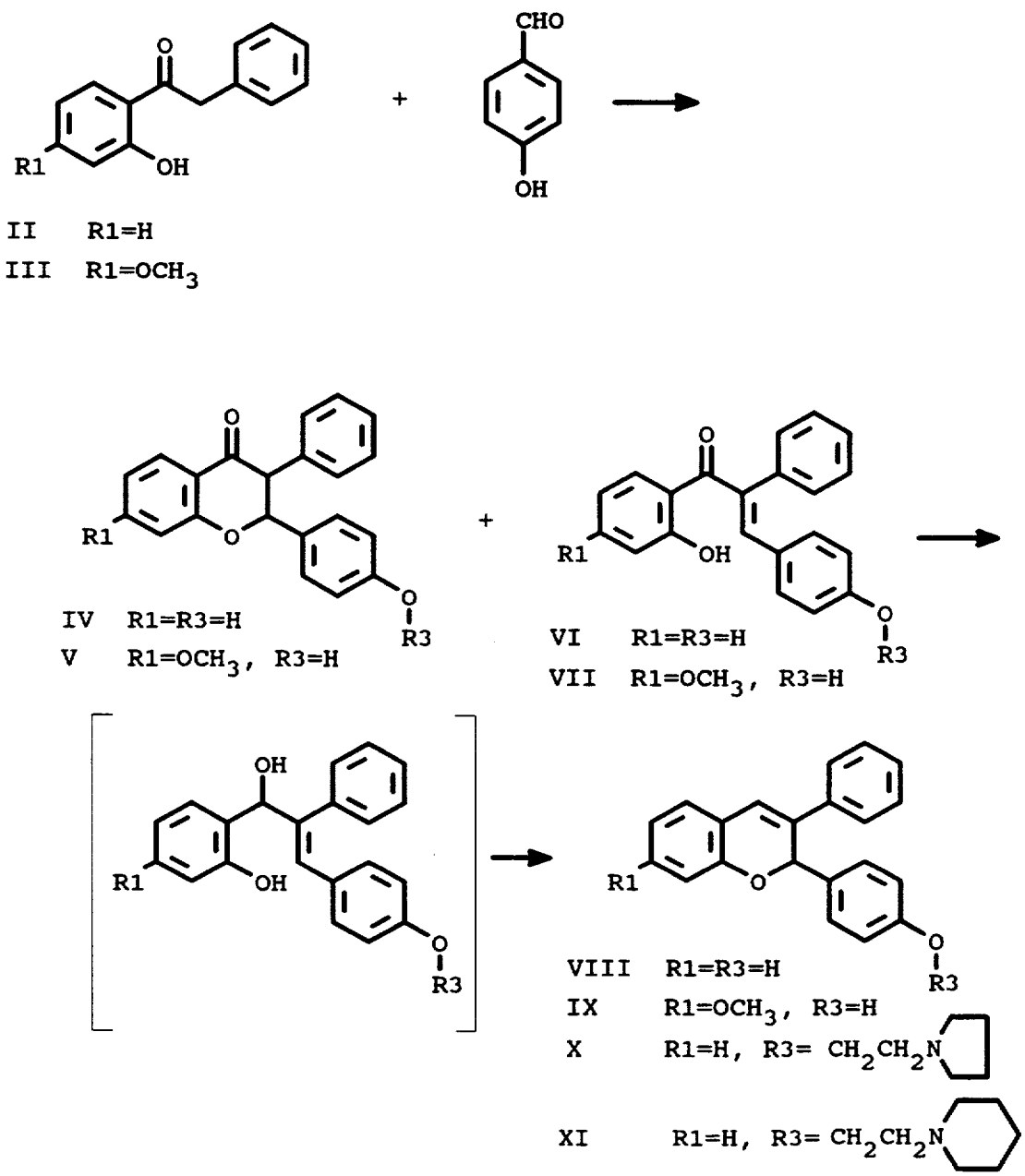
FIGURE

METHOD FOR TREATING DERMATITIS AND RELATED CONDITIONS

BACKGROUND OF THE INVENTION

Dermatitis encompasses a number of conditions characterized by reddish skin lesions that can develop into scaly, thickened plaques. These lesions can arise from any of several primary causes, including contact with allergens, ultraviolet light or chemicals, systemically administered drugs, or localized trauma (irritation). The causes of certain forms of dermatitis are unknown.

Eczematous dermatitis refers to a group of conditions characterized in the initial stages by edematous, oozing plaques that often contain blisters. These lesions are prone to bacterial infection. Fluid leaks into the intercellular spaces in the epidermis, giving it a spongy appearance. Over time, oozing diminishes, and the lesions become scaly as the epidermis thickens (epidermal hyperplasia).

Of particular concern are chronic forms of dermatitis, including psoriasis and the chronic stages of eczematous dermatitis. Psoriasis is characterized by round, thick, dry, reddish patches covered with silvery scales. Psoriasis may be localized or generalized, and in the latter case may become life-threatening. Psoriatic lesions show marked epidermal hyperplasia and hyperproliferation of keratinocytes. The etiology of psoriasis is believed to include hereditary and autoimmune components. Chronic lesions of eczematous dermatitis are clinically and histologically similar to psoriatic plaques.

Cellular proliferation (e.g. proliferation of keratinocytes) is regulated in part by intracellular calcium levels. Changes in intracellular calcium concentrations influence the phosphorylation of proteins, thus influencing proliferation and other cellular processes. One of the molecules that mediates the effect of intracellular calcium levels on protein phosphorylation is calmodulin, a protein co-factor for protein kinase C.

Psoriasis is treated by the application of corticosteroids, coal tar ointments, or anthralin. These treatments are only partially effective and may merely contain, not reverse, the disease. Anthralin may cause irritation, and its safety in children and pregnant women has not been established. Corticosteroids have a number of undesirable side effects, including edema and mineral imbalances. Non-steroidal anti-inflammatory agents are generally not effective.

Certain substituted 2,3-diaryl-1-benzopyrans have been shown to have antiestrogenic activity with little or no estrogenicity, and have been proposed for use in the treatment of breast cancer. See Kapil et al., U.S. Pat. No. 5,254,568; Saeed et al., *J. Med. Chem.* 33: 3210–3216, 1990; Sharma et al., *J. Med. Chem.* 33: 3222–3229, 1990; and Sharma et al., *J. Med. Chem.* ..33: 3216–3222, 1990. These compounds have not previously been shown to have anti-inflammatory properties or to be effective against dermatitis.

There remains a need in the art for treatments for dermatitis that are effective and lack serious side effects. The present invention addresses this need and provides other, related advantages.

DISCLOSURE OF THE INVENTION

Within one aspect, the present invention is directed to methods for treating dermatitis (including psoriasis), including the chronic stages of these conditions, which are characterized by the hyperproliferation of keratinocytes. The present invention makes use of compounds of the formula I:

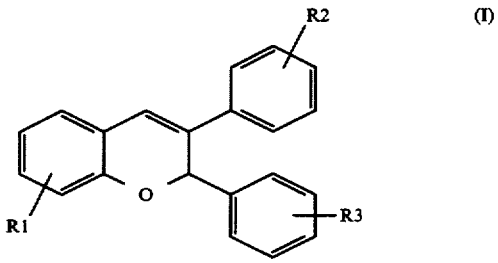

wherein each of R1 and R2 is individually H, OH, linear or branched chain $C_1$–$C_{17}$ alkoxy, linear or branched chain $C_2$–$C_{18}$ acyloxy, or linear or branched chain $C_2$–$C_{18}$ alkoxycarbonyl; and R3 is

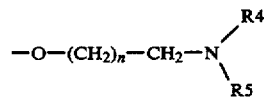

wherein each of R4 and R5 is individually a linear or branched chain alkyl radical of from one to 18 carbon atoms, or together with N, R4 and R5 form a three- to 10-membered ring, and n is an integer from 1 to 6.

Within one embodiment, the present invention provides a method for treating eczematous dermatitis comprising administering to a patient suffering from eczematous dermatitis an effective amount of a composition comprising a compound of formula I or a pharmaceutically acceptable salt thereof in combination with a pharmaceutically acceptable carrier.

Within a related embodiment, the present invention provides a method for treating psoriasis comprising administering to a patient a composition comprising a compound of formula I or a pharmaceutically acceptable salt thereof as described above.

Within another aspect, the present invention provides a method for inhibiting the proliferation of keratinocytes in a patient. Briefly, a compound of formula I or a pharmaceutically acceptable salt thereof in combination with a pharmaceutically acceptable carrier is administered to a patient in an amount sufficient to inhibit keratinocyte proliferation.

Yet another aspect of the present invention provides a method for inhibiting calmodulin activity in a patient comprising administering to the patient a compound of formula I or a pharmaceutically acceptable salt thereof in combination with a pharmaceutically acceptable carrier in an amount sufficient to inhibit calmodulin activity.

These and other aspects of the invention will become evident upon reference to the following detailed description and the attached drawing.

BRIEF DESCRIPTION OF THE DRAWING

The FIGURE illustrates the preparation of certain compounds useful within the present invention.

DETAILED DESCRIPTION OF THE INVENTION

The present invention provides methods for treating dermatitis (including psoriasis), including the chronic stages of these conditions, which are characterized by the hyperproliferation of keratinocytes. The present invention makes use of 2,3-diaryl-1-benzopyrans, which are defined by the general formula I:

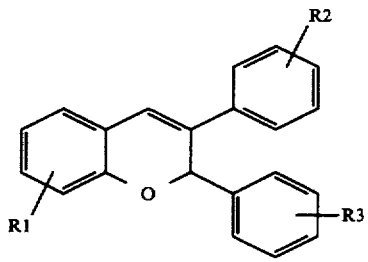

wherein each of R1 and R2 is individually H, OH, linear or branched chain $C_1$-$C_{17}$ alkoxy, linear or branched chain $C_2$-$C_{18}$ acyloxy, or linear or branched chain $C_2$-$C_{18}$ alkoxycarbonyl; and R3 is

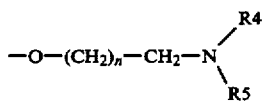

wherein each of R4 and R5 is individually a linear or branched chain alkyl radical of from one to 18 carbon atoms, or together with N, R4 and R5 form a three- to 10-membered ring; and n is an integer from 1 to 6, preferably 1 to 3, most preferably 1. Preferably, each of R4 and R5 is individually methyl, ethyl, propyl, isopropyl, butyl, isobutyl, sec-butyl or tert-butyl, or together with N, R4 and R5 form a five- or six-membered ring. Most preferably, R3 is

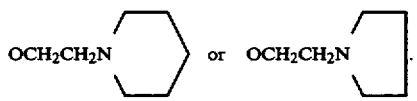

Within preferred embodiments, the compounds I have the structure:

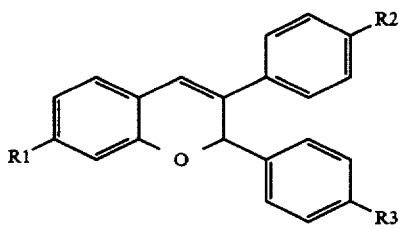

Within other preferred embodiments, R1 and R2 are alkoxy. Within other preferred embodiments, R1 and R2 are individually H, OH or $C_1$-$C_4$ alkoxy, $C_2$-$C_5$ alkoxycarbonyl or $C_2$-$C_5$ acyloxy. R3 is preferably a 2-piperidinoethoxy radical. Within other preferred embodiments, R1 and R2 are individually H or OH. As used herein, the term "acyloxy" refers to radicals of the structure

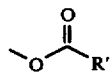

wherein R' is linear or branched chain alkyl or aminoalkyl.

Particularly preferred compounds for use within the present invention include:

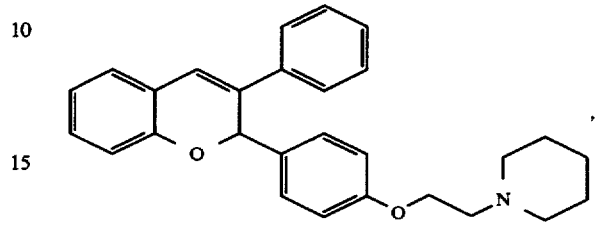

i.e. R1=R2=H and R3 is:

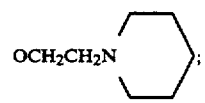

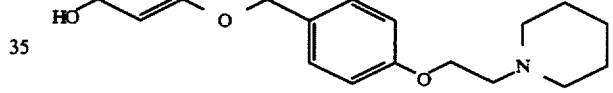

i.e. R1=OH, R2=H, and R3 is:

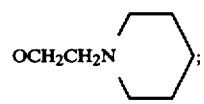

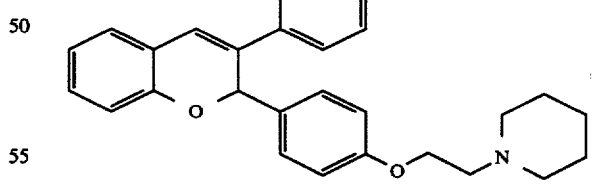

i.e. R1=H, R2=OH, and R3 is:

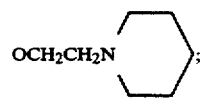

and

-continued

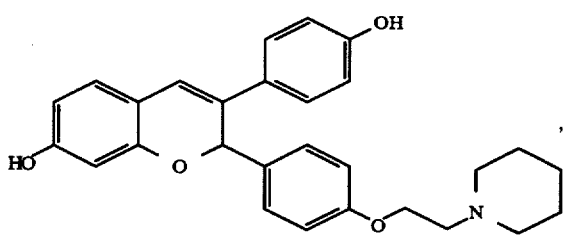

i.e. R1=R2=OH and R3 is:

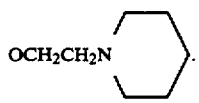

Although it is preferred to use the 2,3-diaryl-2H-1-benzopyrans disclosed above, 2,3-diaryl-1-benzopyrans substituted at the 2 position may also be used to treat dermatitis and related conditions. Preferred substitutions in this regard include methyl, ethyl, propyl and butyl. In addition, each of the aromatic rings of I can be further substituted at one or more positions with a moiety such as OH; fluoro; $CF_3$; CN; a linear alkyl, alkoxy or acyloxy radical of from one to eighteen carbon atoms; a branched alkyl, alkoxy or acyloxy radical of from three to eighteen carbon atoms; $NO_2$; $NH_2$ or NHCOR", wherein R" is a linear or branched chain alkyl radical of from one to eighteen carbon atoms. Those skilled in the art will recognize that substitutions should generally be limited in number and/or size so as not to disrupt the function of the molecule due to large changes in solubility, receptor interactions, biological activity, etc. Thus, substitutions are preferably limited in number and will consist of groups of smaller size, e.g. lower ($C_1$–$C_4$) alkyl radicals.

Benzopyrans of the formula I can be prepared according to the methods disclosed in Saeed et al., *J. Med. Chem.* 33: 3210–3216, 1990; Sharma et al., *J. Med. Chem.* 33: 3222–3229, 1990; and U.S. Pat. No. 5,254,568, which are incorporated herein by reference in their entirety. A representative synthetic scheme is illustrated in FIG. 1. Base-catalyzed condensation of desoxybenzoin II with 4-hydroxybenzaldehyde yields a mixture of the dihydro-4H-1-benzopyran-4-one IV and the 2-phenylchalcone VI. Similarly, condensation of desoxybenzoin III with 4-hydroxybenzaldehyde gives a mixture of the dihydrobenzopyran-4-one V and the 2-phenylchalcone VII. Reduction of the phenylchalcones VI and VII with sodium borohydride followed by thermal cyclodehydration of the alcohols yields the 2H-benzopyran phenols VIII and IX, respectively. Compounds VIII and IX are then alkylated to produce the ethers X and XI, respectively. Hydroxy derivatives of I (i.e. those in which at least one of R1 and R2 is OH) can be prepared as disclosed by Sharma et al. (ibid.) and in U.S. Pat. No. 5,254,568 by condensation of appropriately OTHP (O-tetrahydropyranyl) protected hydroxy derivatives of desoxybenzoin with 4-hydroxybenzaldehyde. Phenolic derivatives having a piperidinoethoxy residue on 2-phenyl are prepared by starting from THP ethers of the appropriate desoxybenzoins, thereby allowing selectivity in attachment of the side chain to the requisite OH group.

Synthesis of 2,3-diaryl-1-benzopyrans substituted at one or more positions on the aromatic rings is carried out using conventional synthetic techniques from suitable precursors, e.g. substituted desoxybenzoins and/or substituted benzaldehydes, such as 4-hydroxy-3-methoxybenzaldehyde, 3,4-dihydroxybenzaldehyde, or 2,4-dihydroxybenzaldehyde.

Within the present invention, 2,3-diaryl-1-benzopyrans may be prepared in the form of pharmaceutically acceptable salts, especially acid-addition salts, including salts of organic acids and mineral acids. Examples of such salts include salts of organic acids such as formic acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulfuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

According to the present invention, the 2,3-diaryl-1-benzopyrans and their salts are used within human and veterinary medicine for the treatment of eczematous dermatitis and psoriasis. "Eczematous dermatitis" includes allergic contact dermatitis, atopic dermatitis, photoeczematous dermatitis and primary irritant dermatitis. The methods of the present invention may be used to treat these conditions in their acute or chronic stages. While not wishing to be bound by theory, it is believed that the therapeutic effect of the 2,3-diaryl-1-benzopyrans is at least in part due to an antagonistic effect on calmodulin, making these compounds particularly effective in the chronic, hyperproliferative stages of eczematous dermatitis and psoriasis.

For use within the present invention, 2,3-diaryl-1-benzopyrans and their pharmaceutically acceptable salts are formulated with a pharmaceutically acceptable carrier to provide a medicament for topical or oral administration according to conventional methods. Formulations may further include one or more diluents, fillers, emulsifiers, preservatives, buffers, excipients, etc. and may be provided in such forms as liquids, ointments, salves, gels, emulsions and the like. One skilled in the art may formulate the compounds in an appropriate manner, and in accordance with accepted practices, such as those disclosed in *Remington's Pharmaceutical Sciences*, 18th ed., Gennaro, ed., Mack Publishing Co., Easton, Pa., 1990 (which is incorporated herein by reference in its entirety.) Such compositions may further include one or more auxiliary substances, such as wetting agents, stabilizers, colorings, penetration enhancers, etc.

Within a preferred embodiment, pharmaceutical compositions are applied topically to skin lesions. Suitable compositions in this regard include oil-based formulations such as ointments, water-in-oil emulsions and solutions of the active agent in a volatile solvent such as an ethanol/ether mixture. Compositions of this type are applied from one to several times daily. Water-based formulations may be applied as wet dressings.

The pharmaceutical compositions may also be administered orally, preferably as tablets or capsules. Oral administration will generally take place at daily to weekly intervals.

An "effective amount" of such a pharmaceutical composition is the amount that provides a clinically significant improvement in the symptoms of the condition to be treated. In particular, it is desirable to achieve a reduction in epidermal hyperplasia and/or keratinocyte hyperproliferation. Determination of such amounts will generally be done empirically and is within the ordinary level of skill in the art. The treatment may be adjusted as necessary to obtain the desired effects, such as by altering the concentration of active ingredient in the formulation or by varying the treatment schedule. The actual amount administered will of course depend in part on the particular condition to be treated (including its extent and severity), age, weight, and general health of the patient, and other factors evident to those skilled in the art. For example, a typical formulation for topical delivery will contain from 0.01 to 10 weight percent of a 2,3-diaryl-1-benzopyran in a suitable vehicle, more preferably from 0.5 to 5 weight percent. The formulation will be applied to the affected skin from one to several times per day until the desired improvement is achieved.

General guidance for treatment regimens is obtained from experiments carried out in animal models of the disease of interest. For example, animal models of psoriasis include the analysis of histological alterations in adult mouse tail epidermis (Hofbauer et al, Brit. J. Dermatol. 118: 85–89, 1988; Bladon et al., Arch Dermatol. Res. 277: 121–125, 1985, incorporated herein by reference). In this model, anti-psoriatic activity is indicated by the induction of a granular layer and orthokeratosis in areas of scale between the hinges of the tail epidermis. Typically, a topical ointment is applied daily for seven consecutive days, then the animal is sacrificed, and tail skin is examined histologically. An additional model is provided by grafting psoriatic human skin to congenitally athymic (nude) mice (Krueger et al., J. Invest. Dermatol. 64:307– 312, 1975, incorporated herein by reference). Such grafts have been shown to retain the characteristic histology for up to eleven weeks. As in the mouse tail model, the test composition is applied to the skin at predetermined intervals for a period of one to several weeks, at which time the animals are sacrificed and the skin grafts examined histologically. A third model has been disclosed by Fretland et al. (Inflammation 14: 727–739, 1990; incorporated herein by reference). Briefly, inflammation is induced in guinea pig epidermis by topically applying phorbol ester (phorbol-12-myristate-13-acetate; PMA), typically at ca. 2 g/ml in acetone, to one ear and vehicle to the contralateral ear. Test compounds are applied concurrently with the PMA, or may be given orally. Histological analysis is performed at 96 hours after application of PMA. This model duplicates many symptoms of human psoriasis, including edema, inflammatory cell diapedesis and infiltration, high $LTB_4$ levels and epidermal proliferation.

Calmodulin activity is conveniently assayed by measuring the activity of calmodulin-dependent enzymes. See, for example, Blumenthal et al., Biochem. Biophys. Res. Comm. 156: 860–865, 1988, which is incorporated herein by reference. Calmodulin-dependent enzymes include phosphorylase kinase, brain multifunctional calmodulin-dependent protein kinase and calmodul-independent protein phosphatase (calcineurin). Phosphorylase kinase activity is determined by measuring rates of $^{32}P$ incorporation into phosphorylase b using a filter paper assay (Roskoski, Methods Enzymol. 99: 3–6, 1983, incorporated herein by reference). A reaction mixture containing 50 mM magnesium acetate, 200 μM $CaCl_2$, 5 mg/ml phosphorylase b, 0.9 μg/ml skeletal muscle phosphorylase kinase, calmodulin, and the test compound are combined. The mixture is incubated at 30° C. for five minutes, and the reaction is initiated by the addition of [γ-$^{32}P$]ATP. Phosphatase activity is assayed by determining rates of $^{32}Pi$ release from a synthetic phosphopeptide corresponding to residues 81–99 of bovine cardiac cAMP-dependent protein kinase regulatory subunit. The reaction mixture contains 50 mM MOPS (4-morpholinepropanesulfonic acid) pH 7.0, 15 mM 2-mercaptoethanol, 2 mM magnesium acetate, 2 mM $MnCl_2$, 0.3 μg/ml bovine brain calmodulin-dependent phosphatase, calmodulin, and the test compound. The mixture is incubated at 30° C. for five minutes, and the reaction is initiated by the addition of $^{32}P$-labeled peptide. Protein kinase activity may be assayed by determining the rate of $^{32}p$ incorporation into chicken gizzard muscle myosin light chain using a filter paper method (Roskoski, ibid.) in a reaction mixture of 50 mM Tris, pH 7.6, 0.6 mM dithiothreitol, 0.6 mg/ml bovine serum albumin (BSA), 80 mM $NaCl_1$, 0.5 mM $CaCl_2$, 1.0 μg/ml kinase, calmodulin and test compound. The reaction is initiated by the addition of Mg-[γ-$^{32}P$]ATP and myosin light chain (40 μM final concentration) at 25° C. Calmodulin concentrations typically range between 1 nM and 1 μM.

Calmodulin is believed to play a pathogenic role in the tissue damage caused by burns and frostbite (Beitner et al., Gen. Pharmac. 2.0: 641–646, 1989), as well as in dermatitis and other conditions involving keratinocyte hyperproliferation. The methods of the present invention may be applied to the treatment of these and other conditions wherein antagonism of calmodulin activity is desirable.

The following examples are offered by way of illustration, not limitation.

EXAMPLE 1

Collodion solvent is added to pure 2-[4-(2-piperidinoethoxy)phenyl]-3-phenyl-2H-1-benzopyran to provide a final concentration of 100 mg per 10 ml of solvent. The solvent is a mixture of three parts by volume of diethyl ether to one part by volume of ethanol. The resulting solution is aliquotted into sterile dropper bottles. For use, the formulation is applied directly to affected skin using a dropper in an amount sufficient to cover the affected area.

EXAMPLE 2

Soft white paraffin BP is heated to 60° C., at which point it melts. 2-[4-(2-piperidinoethoxy)phenyl]-3-phenyl-2H-1-benzopyran is added directly at a concentration of 10 mg per gram of paraffin, and the mixture is thoroughly stirred. After cooling, the formulation is packaged in sterile containers. For use, the formulation is applied by rubbing directly onto affected skin.

Although the foregoing invention has been described in some detail by way of illustration and example for purposes of clarity of understanding, it will be evident that certain changes and modifications may be practiced within the scope of the appended claims.

What is claimed is:

1. A method for treating dermatitis in a patient comprising administering to a patient suffering from dermatitis an effective amount of a composition comprising a compound of the formula

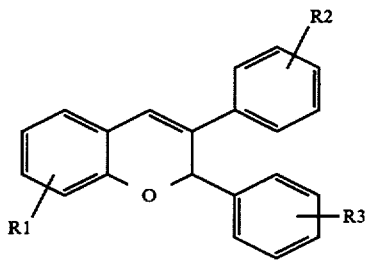

or a pharmaceutically acceptable salt thereof, wherein:
each of R1 and R2 is individually H, OH, linear or branched chain $C_1$–$C_{17}$ alkoxy, linear or branched chain $C_2$–$C_{18}$ acyloxy, or linear or branched chain $C_2$–$C_{18}$ alkoxycarbonyl; and
R3 is

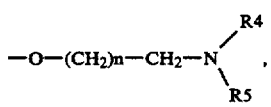

wherein each of R4 and R5 is individually a linear or branched chain alkyl radical of from one to 18 carbon atoms, or together with N, R4 and R5 form a three- to 10-membered ring, and n is an integer from 1 to 6,
in combination with a pharmaceutically acceptable carrier.

2. A method according to claim 1 wherein each of R1 and R2 is individually H, OH or $C_1$–$C_4$ alkoxy.

3. A method according to claim 1 wherein R1 is H or OH.

4. A method according to claim 1 wherein R2 is H or OH.

5. A method according to claim 1 wherein each of R4 and R5 is individually methyl, ethyl, propyl, isopropyl, butyl, isobutyl, sec-butyl or tert-butyl; or together with N, R4 and R5 form a five- or six-membered ring.

6. A method according to claim 1 wherein R3 is

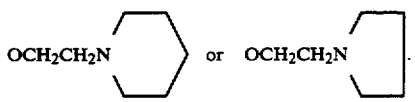

7. A method according to claim 6 wherein each of R1 and R2 is individually H or OH.

8. A method according to claim 1 wherein said compound is

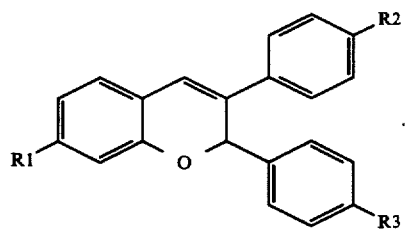

9. A method according to claim 8 wherein each of R1 and R2 is individually H or OH, and R3 is

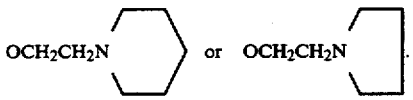

10. A method according to claim 1 wherein said dermatitis is a condition selected from the group consisting of psoriasis and eczematous dermatitis.

11. A method according to claim 10 wherein said condition is psoriasis.

12. A method according to claim 10 wherein said condition is atopic dermatitis, photoeczematous dermatitis, primary irritant dermatitis or allergic contact dermatitis.

13. A method according to claim 1 wherein said composition is in a form suitable for topical administration.

* * * * *